United States Patent
Kobayashi et al.

(10) Patent No.: US 9,339,027 B2
(45) Date of Patent: May 17, 2016

(54) ENHANCEMENT OF ELECTROMAGNETIC FREEZING BY STABILIZATION AND OSCILLATION OF BIOGENIC MAGNETITE PARTICLES

(71) Applicant: CALIFORNIA INSTITUTE OF TECHNOLOGY, Pasadena, CA (US)

(72) Inventors: Atsuko Kobayashi, Tokyo (JP); Joseph L. Kirschvink, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/328,602

(22) Filed: Jul. 10, 2014

(65) Prior Publication Data

US 2015/0037782 A1    Feb. 5, 2015

Related U.S. Application Data (60) Provisional application No. 61/859,940, filed on Jul. 30, 2013.

(51) Int. Cl.
| | | |
|---|---|---|
| *A01N 1/02* | (2006.01) | |
| *A23L 3/36* | (2006.01) | |
| *A23L 3/32* | (2006.01) | |

(52) U.S. Cl.
CPC ............... *A01N 1/0294* (2013.01); *A23L 3/32* (2013.01); *A23L 3/363* (2013.01)

(58) Field of Classification Search
CPC ................................ A01N 1/0294; A23L 3/32
See application file for complete search history.

(56) References Cited

U.S. PATENT DOCUMENTS

| | | |
|---|---|---|
| 1,835,557 A | 12/1931 | Burke |
| 6,250,087 B1 | 6/2001 | Owada et al. |
| 7,237,400 B2 | 7/2007 | Owada |
| 7,810,340 B2 | 10/2010 | Owada et al. |
| 2009/0199577 A1 | 8/2009 | Owada et al. |

OTHER PUBLICATIONS

International Search Report mailed on Nov. 11, 2014 for PCT/US2014/047884 filed on Jul. 23, 2014 in the name of California Institute of Technology.
Written Opinion mailed on Nov. 11, 2014 for PCT/US2014/047884 filed on Jul. 23, 2014 in the name of California Institute of Technology.
S. Abedini, et al., "Effects of cryopreservation with a newly-developed magnetic field programmed freezer on periodontal ligament cells and pulp tissues", Cryobiology, 62 (2011) 181-187.
R.K. Adair, "Constraints on biological effects of weak extremely-low-frequency electromagnetic fields", Phys. Rev. A., 43 (2) (1991) 1039-1048.
P.H.G. Allen, "Electric stress and heat transfer", British Journal of Applied Physics, 10 (1959) 347-351.

(Continued)

*Primary Examiner* — Rosanne Kosson
(74) *Attorney, Agent, or Firm* — Steinfl & Bruno LLP (57) ABSTRACT

Novel methods and systems for electromagnetic freezing are disclosed. An oscillating magnetic field can be applied in conjunction with a static magnetic field in order to align magnetic particles inside biological tissues. Such chains may be naturally present or artificially introduced. Needle-shaped electrodes may be used to produce ions and disturb the air layers insulating the tissues to be frozen.

12 Claims, 2 Drawing Sheets

(56) References Cited

OTHER PUBLICATIONS

E. Bonjour, et al., "Electroconvection effects on heat transfer", Chem. Eng. Prog., 58 (7) (1962) 63-66.

F. Brem, et al., "Magnetic iron compounds in the human brain: a comparison of tumour and hippocampal tissue", Journal of the Royal Society Interface, 3 (2006) 833-841.

H.Y. Choi, "Electrohydrodynamic condensation heat transfer", Journal of Heat Transfer, 90 (1968) 98-102.

J.D. Cobine, "Ch. 19—Other Electrostatic Effects and Applications" in: A.D. Moore, (Ed.), *Electrostatics and Its Applications*, Wiley, New York, (1973) 441-455.

J.F. Collingwood, et al., "Three-dimensional tomographic Imaging and characterization of iron compounds within Alzheimer's plaque core material", Journal of Alzheimer's Disease, 14 (2008) 235-245.

J. Dobson, et al, "Magnetic properties of human hippocampal tissue—evaluation of artefact and contamination sources", Brain Research Bulletin, 39 (4) (1996) 255-259.

J.R. Dunn, et al. "Magnetic material in the Human hippocampus", Brain Research Bulletin 36 (2) (1995) 149-153.

S.H.K. Eder, et al., "Magnetic characterization of isolated candidate vertebrate magnetoreceptor cells", Proceedings of the National Academy of Sciences of the United States of America, 109 (30) (2012) 12022-12027.

J.L. Gould, et al., "Bees have magnetic remanence", Science, 201 (4360) (1978) 1026-1028.

P.P. Grassi-Schultheiss, et al., "Analysis of magnetic material in the human heart, spleen and liver", BioMetals, 10 (1997) 351-355.

D. Gunders, "Wasted: How America is Losing Up to 40 Percent of Its Food from Farm to Fork to Landfill", NRDC Issue Paper Natural Resources Defense Council, (2012) 26 pages.

D. Hautot, et al., "Preliminary observation of elevated levels of nanocrystalline iron oxide in the basal ganglia of neuroferritinopathy patients", Biochimica Et Biophysica Acta, 1772 (2007) 21-25.

D. Hautot, et al., "Superconducting quantum interference device measurements of dilute magnetic materials in biological samples", Review of Scientific Instruments, 76 (2005) 045101-1 to 045101-4.

M. Kaku, et al., "Cryopreservation of periodontal ligament cells with magnetic field for tooth banking", Cryobiology, 61 (2010) 73-78.

M. Kaku, et al., "Electric and magnetic fields in cryopreservation: A response", Cryobiology, 64 (2012), 304-305.

J.L. Kirschvink, et al., "Biogenic magnetite as a basis for magnetic field detection in animals", BioSystems, 13 (1981) 181-201.

J.L. Kirschvink, et al., "Comment on 'Constraints on biological effects of weak extremely-low-frequency electromagnetic fields'", Physical Rev. A., 46 (4) (1992) 2178-2184.

J.L. Kirschvink, et al., "Magnetite-based Magnetoreception", Current Opinion in Neurobiology, 11 (2001) 462-467.

J.L. Kirschvink, et al., "Magnetite biomineralization in the human brain", Proceedings of the National Academy of Sciences, 89 (1992) 7683-7687.

J.L. Kirschvink, "Rock Magnetism linked to Human Brain Magnetite", EOS, Trans. Am. Geophysical Union, 75 (15) (1994) 178-179.

A. Kirschvink-Kobayashi, et al., "Electrostatic enhancement of industrial drying processes", Ind. Engin. Chem. Proc. Design & Develop., 25 (4) (1986) 1027-1030.

A. Kobayashi, et al, "Ch. 21—Magnetoreception and Electromagnetic Field Effects: Sensory Perception of the Geomagnetic Field in Animals & Humans" (in M. Blank, (Ed.), *Electromagnetic Fields: Biological Interactions and Mechanisms*, American Chemical Society Books, Washington, D.C.) (1995) 367-394.

A. Kobayashi, et al, "Experimental observation of magnetosome chain collapse in magnetotactic bacteria: Sedimentological, paleomagnetic, and evolutionary implications", Earth and Planetary Science Letters, 245 (2006) 538-550.

A.K. Kobayashi, et al., "Ferromagnetism and EMFs", Nature, 374 (1995) 123.

A.K. Kobayashi, et al., "Studies of inorganic crystalline solid in biosystem—magnetite in the Human Body", J. Japanese Society of Powder and Powder Metallurgy, 43 (11) (1996) 1354-1360. English abstract only; Examiner cannot read Japanese.

A.K. Kobayashi, et al., "Studies of inorganic crystals in biological tissue: magnetite in human tumor", J. Japanese Society of Powder and Powder Metallurgy, 44 (1997) 294-300.

R. Kronig, et al., "On the theory of heat transfer from a wire in an electric field", Applied Scientific Research Section a-Mechanics Heat Chemical Engineering Mathematical Methods, 1 (1947) 35-46.

S.Y. Lee, et al., "Magnetic Cryopreservation for Dental Pulp Stem Cells", Cells Tissues Organs, 196 (2012) 23-33.

P.Y. Lin, et al., "Cryopreservation of human embryonic stem cells by a programmed freezer with an oscillating magnetic field", Cryobiology, 66 (2013), 256-260.

H.A. Lowenstam, "Magnetite in denticle capping in recent chitons (polyplacophora)", Geol. Soc. Am. Bull., 73 (1962) 435-438.

P.S. Lykoudis, et al., "The influence of electrostrictive forces in natural thermal convection", International Journal of Heat and Mass Transfer 6 (1963) 853-862.

E.B. Moore et al., "Structural transformation in supercooled water controls the crystallization rate of ice", Nature, 479 (2011) 506-508.

M. Naito, et al., "Effect of a Magnetic Field on Drosophila under Supercooled Conditions", Plos One 7 (2012) 5 pages.

Q. Pankhurst, et al., "Increased levels of magnetic iron compounds in Alzheimer's Disease", Journal of Alzheimer's Disease, 13 (2008) 49-52.

M. Robinson, "Convective heat transfer at the surface of corona electrode", International Journal of Heat and Mass Transfer, 13 (1970) 263-274.

T. Suzuki, et al., "Experimental Investigation of Effectiveness of Magnetic Field on Food Freezing Process." Transactions of the Japan Society of Refrigerating and Air Conditioning Engineers, 26 (4) (2009) 371-386. English Summary Only; Examiner cannot read Japanese.

C. Walcott, et al., "Pigeons have magnets", Science, 205 (1979) 1027-1029.

M.M. Walker, et al., "A candidate magnetic sense organ in the Yellowfin Tuna *Thunnus albacares*", Science, 224 (1984) 751-753.

M.M. Walker, et al., "Ch. 5—Detection, Extraction, and Characterization of Biogenic Magnetite" (in J.L. Kirschvink, et al., *Magnetite Biomineralization and Magnetoreception in Organisms: A New Biomagnetism*, Plenum Press, New York, N.Y.) (1985) 155-166.

M.M. Walker, et al., "Ch. 20—Magnetoreception and Biomineralization of Magnetite Fish" (in J.L. Kirschvink, et al., *Magnetite Biomineralization and Magnetitoereception in Organisms: A New Biomagnetism*, Plenum Press, New York, N.Y.), 1985, 417-437.

M.M. Walker, et al., "Production of single-domain magnetite throughout life by sockeye salmon, *Oncorhynchus nerka*", J. Exptl. Biol., 140 (1988) 51-63.

B. Wowk, "Electric and magnetic fields in cryopreservation", Cryobiology, 64 (2012), 301-303.

ENHANCEMENT OF ELECTROMAGNETIC FREEZING BY STABILIZATION AND OSCILLATION OF BIOGENIC MAGNETITE PARTICLES

CROSS REFERENCE TO RELATED APPLICATIONS

The present application claims priority to U.S. Provisional Patent Application No. 61/859,940, filed on Jul. 30, 2013, the disclosure of which is incorporated herein by reference in its entirety.

TECHNICAL FIELD

The present disclosure relates to electromagnetic freezing and enhancement of electromagnetic freezing by the application of magnetic fields that cause the elliptically to circularly-polarized oscillation of tiny magnetic particles (usually biogenic magnetite), inhibiting the nucleation of ice crystals on their surface. More in particular, it relates to enhancement of electromagnetic freezing by stabilization and oscillation of biogenic magnetite particles.

SUMMARY

In a first aspect of the disclosure, a system to freeze biological tissues is described, the system comprising: a container, configured to contain biological tissues; a static magnetic field generator, configured to apply a static magnetic field to biological tissues in the container; an oscillating magnetic field generator, configured to apply an oscillating magnetic field to the biological tissues in the container; a freezing element, configured to freeze the biological tissues in the container.

In a second aspect of the disclosure, a method to freeze biological tissues is described, the method comprising: providing a refrigerating container, configured to contain and freeze biological tissues; aligning magnetic particles in biological tissues by applying a static magnetic field to the biological tissues in the container; vibrating the magnetic particles in the biological tissues by applying an oscillating magnetic field to the biological tissues in the container, wherein the oscillating magnetic field is perpendicular to the static magnetic field; freezing the biological tissues while the static and oscillating magnetic fields are active.

In a third aspect of the disclosure, a method to freeze biological tissues is described, the method comprising: providing a refrigerating container configured to contain and freeze biological tissues, the refrigerating container having a plurality of needle-shaped electrodes pointing at the biological tissues, the needle-shaped electrodes being substantially close to, but separated from, the biological tissues; aligning magnetic particles in the biological tissues by applying a static magnetic field to the biological tissues in the container; vibrating the magnetic particles in the biological tissues in an elliptical or circular manner by applying an oscillating magnetic field to the biological tissues in the container, wherein the oscillating magnetic field is perpendicular to the static magnetic field with a component of rotation around it; applying a voltage difference between the needle-shaped electrodes and the biological tissues, thereby producing ions in an air layer surrounding the biological tissues; freezing the biological tissues while the voltage difference and the static and oscillating magnetic fields are active.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The present disclosure relates to enhancement of electromagnetic freezing by the application of magnetic fields that cause the elliptically to circularly-polarized oscillation of tiny magnetic particles (usually biogenic magnetite), inhibiting the nucleation of ice crystals on their surface.

Throughout the present disclosure, embodiments and variations are described for the purpose of illustrating uses and implementations of the inventive concept. The illustrative description should be understood as presenting examples of the inventive concept, rather than as limiting the scope of the concept as disclosed herein. Like reference numerals indicate corresponding parts in various figures.

Freezing is an important technological process in a variety of fields, including but not limited to the food industry. Freezing reduces the time rate of biological and chemical processes, therefore it can be used, for example, to reduce the rate of microbial activity which spoils food consumable by humans or animals.

The amount of loss of human food resources between the agricultural fields and the table can be up to 40% (even for an advanced technological country as the United States), (see, for example reference [50]). Any improvements in our ability to reduce this waste could have profound implications for the sustainable future of humanity. Refrigeration and freezing technologies can have difficulty in preserving plant and animal tissues for shipping because of the damage that ice crystals produce when the material freezes. For example, freezing fruits and vegetables is a particular problem. Recently, the company ABI in Chiba, Japan has been marketing a "cells alive system" (CAS) which is claimed to greatly reduce the problem of cells being disrupted by growing ice crystals. The CAS system employs a combination of conventional freezer technology coupled with selected oscillating electrical and magnetic fields, as well as the application of sound waves. The ABI Corporation claims to have improved the ability to freeze much larger volumes of animal and vegetable matter with minimal damage to cellular ultrastructure from ice crystal growth. The programmable CAS freezers expose samples to low-frequency oscillating electric and magnetic fields, and weak sound, while controlling the supercooling of the materials in the critical temperature interval from 0° C. to −20° C. by blowing refrigerated air on the samples (see, for example, references [1], [2], and [3]).

However, publicly available descriptions of the reason why the CAS system may be effective in freezing biological tissues, while substantially avoiding the formation of ice crystals, violate fundamental principles of thermodynamics and statistical mechanics. For example, a publicly available description asserts that the weak, oscillating magnetic fields are causing water molecules to vibrate, preventing ice crystal nucleation. However, such claims cannot be possible because water molecules are diamagnetic, and the effect of such oscillating magnetic field is many, many orders of magnitude below the background thermal noise. At least one peer-reviewed comment (for example, see reference [9], incorporated herein in its entirety) and reply (for example, see reference [1], incorporated herein in its entirety) have addressed this issue, with no clear resolution. In any event, the freezers appear to work and are being used widely now, even on-board fishing vessels to preserve the taste of the most expensive tuna.

As described in the exemplary embodiments of the present disclosure, discoveries made at Caltech, which started over 50 years ago by the (late) Professor of Paleoecology, Heinz Lowenstam may be related to the way the CAS system operates. Specifically, Lowenstam discovered that the teeth of a primitive group of mollusks, for example, the chitons, were capped by a layer of biologically-precipitated magnetite crystals ($Fe_3O_4$). The mineral is a biological precipitate, in much the same way that human bodies make the mineral apatite in bones and teeth. However, it is the only known biomaterial in animals that is ferromagnetic, i.e., it will be strongly attracted to a magnet. Since Lowenstam's original discovery, numerous studies have shown that the biological precipitation of magnetite is rather common and it occurs in the magnetotactic bacteria and many groups of eukaryotes, including protists and plants, and in a variety of animals including fish, amphibians, reptiles, birds, and mammals. The Kirschvink group at Caltech has shown that the biologically-precipitated magnetite crystals ($Fe_3O_4$) are present in tissues from the human body, and even in some cancer tissues, at levels of up to a few parts per million. Similar levels are present in most animal tissues, as well as in a variety of bacteria and protists, and perhaps plants. Although a few parts per million may appear to be a small quantity, there are many of these clusters in typical tissues, for example, on the order of 100,000 per gram, in the human brain.

Of importance for cryopreservation analysis of biological tissues is the fact that all of the magnetic crystals present in biological tissues interact very strongly (for example, in some cases up to thousands of times above the thermal noise limit) with the magnetic field, at levels and frequencies that are used in the cryopreservation refrigeration systems (such as, the CAS freezers). By contrast, the magnetic interactions of diamagnetic particles are below the thermal noise limit.

The presence of ferromagnetic materials appears to be the only mechanism that can physically account for what is happening in the tissues during freezing, although it has not been mentioned as a possible mechanism in any of the publicly available literature. Additionally, past studies have demonstrated that ferromagnetic contaminants are present in many of the liquid culture media that are used to grow mammalian cell lines in biology research, for which the CAS technique is claimed to enhance survivability. Therefore, such ferromagnetic contaminants may act in a way similar to the ferromagnetic clusters naturally present in biological tissues.

It is known in the art that whenever an underlying physical mechanism is clarified for an industrially-important process that the new understanding offers possible insights for improvement of the related technological methods. Several new opportunities for such improvements are presented and discussed below in the present disclosure.

It is known that the clusters of biological magnetic crystals found in bacteria and animal tissues tend to clump together soon after cell death to reach their minimum-energy configuration. The cytoskeletal proteins that hold the magnetic crystals degrade rapidly after cellular death, allowing them to clump. The clumps are comparatively less effective than isolated magnetic particles or chains in allowing the surrounding liquid to vibrate in phase. The clumps are considerably less effective for at least two reasons: (1) their magnetic moments are reduced (reducing the magnetic torque they feel), compared to the chains, and (2) the surface area of a clump that can transmit acoustic vibrations to the surrounding tissue is much less than what the particles have when strung out in a long chain.

As a consequence, preventing the clumping of the particles prior to freezing would enhance the electromagnetic freezing effect. The present disclosure describes novel methods for enhancing electromagnetic freezing using a static magnetic field, for example, greater than 15 mT. Such a magnetic field can prevent the magnetic particles from clumping, by keeping them strung out, like iron filings near a hand magnet. Based on the methods described in the present disclosure, several types of magnetic pre-treatment for enhancement of cryoprotection prior to freezing can be developed.

Electromagnetic freezing techniques, such as the CAS technique, can be used to cryopreserve many 'liquid' tissues like blood, semen, human eggs, fertilized embryos, and cell cultures. According to the exemplary embodiments of the present disclosure, the addition of suitably tailored ferromagnetic particles could improve the efficiency of electromagnetic freezing techniques by increasing the density of magnetic vibrating sites that would act to inhibit the ice crystal formation process, and correspondingly increase the number of point nucleation sites when the initiation of freezing is desired. Therefore, adding ferromagnetic particles, additional to ferromagnetic clusters naturally present in biological tissues, can enhance cryopreservation methods and systems.

In cases where there are some biological tissues that do not possess enough magnetic material to promote their cryopreservation, or are unsuitable for receiving a sufficient quantity of additional ferromagnetic particles, genetic engineering can be used to turn on the transcription factors that control the formation of the natural, magnetite-precipitating cells in most groups of animals and plants. By turning on the appropriate factors, a higher quantity of natural oscillatory magnetic clusters could be produced, that can inhibit ice crystal nucleation during electromagnetic freezing.

In the patent literature pertaining to electromagnetic freezing (CAS), it is argued that weak sound levels applied to the biological tissues to be frozen are disturbing a surface boundary layer of inert air that normally provides a little bit of thermal insulation at the surface of solids and liquids. Therefore, it is argued that sound waves remove this boundary layer which provides insulation and improve the freezing process.

However, the exemplary embodiments of the present disclosure, as described in the following sections, show that such explanation is not scientifically sound. In fact, heat transport during electromagnetic freezing with applied sound waves is a result of an electrostatic 'corona' wind effect. The electrostatic corona wind effect could be enhanced by the addition of an array of needle electrodes (for example, see reference [11]). The array of needle electrodes could apply a high-voltage electric field and maximize the electrostatic corona effect by generating more ions to move the air that surrounds the biological tissues to be frozen. Therefore, needle electrodes could be used to increase heat transport in electromagnetic freezers. In other words, as known to a person skilled in the art, the needle electrodes generate ions due to electrostatic effects. In such cases pointed electrodes create a localized electrostatic field of higher value, where ions are more likely to be created. The movement of the ions in the electrostatic field can then disturb the air layer around the biological tissues to be frozen.

The possible inhibitory action of electromagnetic fields on ice nucleation and crystallization during cryopreservation can be the starting point of several industrial methods. These methods can originate a major advance in global food-storage techniques. For example, strong electric fields can disrupt the surface boundary layer of inert air on the surface of materials that need to be frozen (e.g. as biological tissues), thus promoting higher rates of evaporation and greater heat transport.

Moreover, as noted above, most biological tissues contain trace amounts of ferromagnetic materials, both biologically precipitated magnetite ($Fe_3O_4$) as well as environmental contaminants that are accidentally incorporated into living systems. Although, present at trace levels, the number density of these particulates can be high, and they can have extraordinarily strong interactions with weak, low-frequency magnetic fields. As known in the art, such weak low-frequency magnetic fields may be used in electromagnetic cryopreservation.

The exemplary embodiments of the present disclosure describe how low-frequency acoustic waves produced by the oscillating ferromagnetic clusters in biological tissues may cause the inhibition of ice crystal nucleation, while allowing tissues to reach supercritical states before crystallization sets in. In such a way, biological tissues can be better preserved, as it is known to a person skilled in the art that crystallization may damage biological tissue and degrade their status upon defreezing.

In some embodiments, pre-treatment of fresh tissues with strong, static magnetic fields may enhance freezing by inhibition and reversal of magnetosome chain collapse. Subsequently, the simultaneous application of oscillating and static magnetic fields may preserve magnetosome chains. Specifically, a magnetic field rotating at a low-frequency perpendicular to a static magnetic field with a higher intensity than the oscillating field can be advantageously applied to biological tissues to preserve chains of magnetic particles, thereby improving the freezing of biological tissues.

As known to the person skilled in the art, magnetosomes are membrane-bound structures present in magnetotactic microorganisms. They are able to orient along the magnetic field lines of Earth's magnetic field, due to the permanent magnetic dipole moment of their encapsulated single-domain magnetite crystals, which are spontaneously ferrimagnetic. Individual cells can contain from a single to thousands of discrete magnetosomes, depending on the species or tissues. Each magnetite crystal within a magnetosome is surrounded by a lipid bilayer, and specific soluble and transmembrane proteins are sorted to the membrane. In the present disclosure, "magnetosome" may be used as a general term to indicate any magnetic particle or cluster of magnetic particles that are present in biological tissues, whether naturally or artificially introduced.

As known to the person skilled in the art, water expands in volume when freezing, from the liquid to the solid state. Water volume expands about 10% upon freezing. This expansion of water when turning into ice can destroy cell membranes by the simple expansion effect, coupled with the damaging effect of sharp edges from the growing ice crystallites. As known to the person skilled in the art, the damage caused by water freezing inside cellular membranes can be avoided by supercooling the water, chilling it to a glassy state that does not go through the expansion process, and/or limiting the size of the ice crystals that do form. Electron microscopists usually are able to achieve this on small samples of a few $mm^3$ by direct immersion in cryogenic liquids, sometimes at high pressure. However, the slow rate of heat conduction inwards into a biological tissue limits the size of tissues that can be preserved in this fashion.

As noted above in the present disclosure, freezing gram-sized or larger objects, such as mouse brains, vegetables, or intact fish, (while retaining the cellular ultrastructure) has been a challenging problem. As also noted above, electromagnetic freezing, such as the CAS technology, can aid in the shipping of delicate fruits and vegetables, and in the enhanced cryopreservation of human transplant tissues like teeth (see, for example, references [4] & [5]) and embryonic stem cells (see, for example, reference [6]). Electromagnetic freezing can also promote whole-organism survival of small animals like drosophila (see, for example, reference [7]) when frozen. Such studies argue that the electromagnetic freezing is a genuine improvement in humanity's ability to use refrigeration to preserve and transport animal and vegetable tissues.

On the other hand, as noted above in the present disclosure, the papers and patents published by the ABI group (see, for example, references [1], [2], [3], and [8]) regarding the CAS system postulate two mechanisms of action that do not agree with basic biophysics. Specifically, a first argument presented in references [1], [2], [3] and [8] states that the oscillating electric and magnetic fields are supposed to directly 'wiggle' water molecules to inhibit the nucleation of ice crystals in the supercooled state, as well as promoting rapid and isothermal cooling of the sample interiors. Additionally, the second argument presented in references [1], [2], [3] and [8] states that weak sounds are supposed to enhance heat conduction into the samples by disrupting the thermal boundary layers of inert air.

Regarding the first argument (magnetic field 'wiggling'), Wowk (see, for example reference [9]) pointed out that, as known to the person skilled in the art, water molecules are diamagnetic and will not produce any effect above thermal noise when exposed to the weak oscillating magnetic fields (e.g. less than 10 Gauss or 1 mT) used in the CAS freezers. Wowk (see, for example reference [9]) also notes that electric fields are known to either inhibit or enhance ice crystal formation slightly, depending upon the conditions used, but not at the levels claimed for these devices.

In a direct test of the magnetic aspect of the CAS freezers, Suzuki et al. (see, for example reference [10]) also report that the application of oscillating magnetic fields alone did not alter the cooling time curves for test samples of radish or sweet potatoes, and had no visible effect on cellular microstructures of the tissues they examined.

As known to the person skilled in the art, if results are not reproducible, then a different scientific explanation might be warranted. Such different scientific explanation is described in the present disclosure and can enable improvements that would not be possible based on incorrect scientific explanations.

Regarding the second argument (i.e. application of sounds to disturb the air layer) an analysis of the sound levels involved in the CAS system (e.g. as seen in Table 1 of the present disclosure) shows that the energy reaching individual water molecules, even at its strongest intensity (10 $W/m^2$), during one vibration cycle, is many orders of magnitude below the energy of thermal noise. As seen in Table 1, the sound levels are also well below the levels of ambient noise in most human environments. Hence, the proposed sonic disruption of the thermal boundary layer at the surface of the sample, as presented by the ABI group in references [1], [2], [3], and [4], is not likely to be correct. Moreover, as known to the person skilled in the art, acoustic vibrations are also supposed to be one of the triggers that can cause supercooled water to crystallize suddenly. Such phenomenon is not consistent with electromagnetic freezing as described in the CAS systems (see, for example, references [2], [3]).

TABLE 1

Order of magnitude energetic analysis of the sound wave component
of CAS freezers at standard temperature and pressure (STP)

| | | |
|---|---|---|
| 3.8E−21 | Joule/kT | One Dimensional thermal background energy, kT |
| 9.6E−11 | m | Approximate size of water molecule |
| 9.2E−21 | m$^2$ | Cross Sectional area of water molecule |
| 6.8E−08 | m | Mean free path of molecules in air at STP |
| 3.0E−26 | kg | Mass of individual water molecule |
| 614 | m/s | Velocity (rms) of water molecule at STP = sqrt(3 kT/mass) |
| 1.1E−10 | seconds | Average time between collisions |
| | | For the weak sound case: |
| 1.0E−10 | W/m$^2$ | Minimum energy of sound from speakers |
| 9.2E−31 | W | Acoustic energy flux from sound on one water molecule, (area × power) |
| 1.0E−40 | Joule | Total acoustic energy 'received' between adjacent collision events, in Joules (flux × intercollision time) |
| 2.7E−20 | kT | Total acoustic energy 'received' between adjacent collision events, in units of kT |
| | | For strong sound case |
| 1.0E+01 | W/m$^2$ | Minimum energy of sound from speakers |
| 9.2E−20 | W | Acoustic energy flux from sound on one water molecule, (area × power) |
| 1.0E−29 | Joule | Total acoustic energy 'received' between adjacent collision events, in Joules (flux × intercollision time) |
| 2.7E−09 | kT | Total acoustic energy 'received' between adjacent collision events, in units of kT |

Electrostatic Effects on Heat Transport

As described in the present disclosure, electrostatic effects on heat transport and biologically-precipitated ferromagnetic materials have a direct bearing on possible solutions to the biophysical puzzle as to why this freezing technology might work, and may lead to improvements in electromagnetic freezing techniques.

In reference [11], the effect of electrostatic fields on the rate of drying of wet materials was studied. It is known to the person skilled in the art from the study of transport phenomena, that a thin layer of relatively inert air exists at the surface of most materials where the relative velocity of gas flow asymptotically drops to zero. As described in references [12], [13], and [14], these surface boundary layers both interfere with the diffusion of gases out of the material and limit the rate of convective heat transfer into it.

It is known to the person skilled in the art that a sharp conducting point will produce an electric or "corona" wind as a result of ions leaving the electrode end point, and this ionic wind can cause a marked increase in heat conduction at a surface by disrupting the stagnant surface boundary layer (see, for example, references [15], [16], [17], [18], [19], and [20]). This effect has been used previously to increase the cooling rate of hot surfaces during welding, for example, to cool semiconductor elements, and to cool optical components in $CO_2$ lasers (see, for example, reference [18]). Compared to the energetics of sound disruption, this electrostatic effect per ion is several orders of magnitude above thermal noise, as outlined in Table 2 of the present disclosure.

Electrostatic fields comparable to those used in CAS freezers are able to disrupt the inert surface boundary layer of air molecules and dramatically shorten drying times [11]. Through a similar effect, the high-voltage electrostatic fields applied in the CAS freezers are increasing cooling efficiency by disrupting the surface boundary layer of inert gas at the surface of their materials. The cooling enhancements shown by Owada et al. [2] are, in fact, similar in style to those reported previously [11]. Hence, either DC or AC high-voltage electric fields would be expected to promote rapid heat removal needed for supercooling, but generation of AC fields is certainly easier with the use of transformers. The addition of spiked shapes on the electrodes might enhance the cooling of the CAS effect by promoting mobile ion formation, as previously observed [11].

TABLE 2

Order of magnitude energetic analysis of the electrostatic component
of CAS freezers at standard temperature and pressure (STP)

| | | |
|---|---|---|
| 1.6E−19 | J | One electron volt |
| 0.001 | m | Approximate thickness of interboundary layer |
| 100 | kV/m | Minimum AC electric field strength used in CAS freezer |
| 100 | volts | Electric field across surface boundary layer |
| 1.6E−17 | J | Energy gained by a single charged ion moving across boundary layer |
| 4243 | kT | Electrostatic energy for charged molecule to be dragged through thermal boundary layer |

Biologically-Precipitated Ferromagnetic Materials

An intrinsically more interesting question concerns the possible mechanism of action of the weak, oscillating magnetic fields on cryopreservation. As known in the art, there are only four possible physical coupling mechanisms that can yield interaction effects between oscillating magnetic fields and matter. For example, electrical induction, diamagnetism, paramagnetism, and ferromagnetism. However, for low-frequency fields weaker than a few hundred μT, only ferromagnetism will work, as the other mechanisms have peak interaction energies well below the thermal noise limit (see, for example, reference [21] for a review of such mechanisms).

In contrast, particles of ferromagnetic materials can have interaction energies hundreds to thousands of times stronger than the background thermal energy (see, for example, reference [22]). Moreover, Owada et al. [2, 3] and Wowk [9] did not consider the well-known presence of ferromagnetic materials, principally biologically-precipitated magnetite ($Fe_3O_4$), in a wide range of biological tissues (see, for example, references [23], [24], [25], [26], [27], [28], and [29]). These observations, which have been widely replicated (see, for example, references [30], [31], [32], [33], [34], [35], [36]), strongly support the hypothesis that some of the ferromagnetic materials are the basis of the magnetic sensory organelles in animals (see, for example, references [37] and [38]). Additionally, brain tissues in humans have been studied extensively (see for example, references [30], [31], [32], [35], [36], [39], [40], [41]). However, as shown in the references [42] and [43], magnetite deposits in specialized cells have been found to be extensive.

On occasion, some ferromagnetic materials of inorganic origin, which are also ubiquitously present in the environment (see, for example, reference [44]), can work their way into biological tissues (see, for example, reference [45]). Typical animal tissues have background concentrations of ferromagnetic materials in the 1-1000 ng/g range, with typical levels of about 4 ng/g. Tissues with elevated levels are thought to host cells involved in magnetoreception, while others might be related to iron storage products, or perhaps even have a role in magnetochemistry (see, for example, reference [46]). As known to the person skilled in the art, the ability on the part of animals to sense magnetic fields has been demonstrated relatively recently. For example, migrating birds have been demonstrated to possess magnetoreception organs.

A recent high-resolution study of cells containing biological magnetite in fish by Eder et al. (see, for example, reference [47]), demonstrated that the individual cells are surprisingly magnetic, with magnetite concentrations often 100 times greater than typical cells of magnetotactic bacteria. These cells have interaction energies of up to 1500 times larger than the background thermal noise in the geomagnetic field. As known to the person skilled in the art, the background thermal energy is of the order of kT, where k is the Boltzmann constant and T the absolute temperature. The interaction energies, which are 1550 larger than the thermal noise as mentioned above, would be on the order of 4,500 times larger than kT in the typical magnetic fields (0.15 mT) used in the CAS freezers (see, for example, reference [1]).

Research work performed on human tissues [39] has reported the presence of about 4 ng/g of magnetite in the cortex and cerebellum (i.e. with a factor of 10× larger in the meninges). These values are similar to those measured with superconducting magnetometry in a variety of other animal tissues (see, for example, reference [27]). With Vertebrate cell concentrations at levels as measured in the literature cited above, minimum estimates are obtained of nearly 100,000 of these cells per gram of typical tissue (see Table 3 of the present disclosure).

TABLE 3

Estimated average spacing of magnetosome clusters in tissue samples

| | | |
|---|---|---|
| 4E−09 | g | Typical magnetite in animal tissues, per gram |
| 4.0 | fA/m$^2$ | Magnetic dipole moment of smallest trout magnetocyte |
| 4.3E−14 | g | Mass of single#domain magnetite per trout magnetocyte |
| 92000 | #/g, or #/cc | Number of magnetocytes per gram of tissue |
| 45 | #/cm | Average number of magnetite clusters along 1 cm |
| 22 | µm | Average spacing between magnetite clusters |

In turn, such research implies that the average distance of any cell within a magnetite-bearing tissue can be on the order of 20 µm from a ferromagnetic cluster. Smaller particle sizes can imply correspondingly more particles, and shorter distances, from the nearest cluster.

Improvements on Electromagnetic Freezing

According to the present disclosure, the electrostatic enhancement observed during the CAS freezing process is a simple disruption of the surface boundary effect of inert air, with as a consequence, more efficient, heat transport process. The enhanced removal of heat from the tissues may be one factor in producing the supercritical cooling observed. Subsequently, enhancing the freezers with an array of sharp needle points to promote the generation of a Corona wind might enhance this effect, as observed in earlier studies (see, for example, reference [11]).

In an attempt to test components of the CAS hypotheses, Suzuki et al. (see, for example, reference [10]) investigated only the claim that the magnetic treatment was involved with heat transport. Such claim was proved to be incorrect, since no magnetic effects were observed in the time/temperature curves of the test components. If the oscillation of microns-scale ferromagnetic particles distributed through tissues is involved in the reported action of CAS freezers, then maybe there are two possible mechanisms for the inhibition of ice crystal nucleation.

First, and most obvious, is the possibility that these particles normally act as some of the nucleation sites for the formation of ice crystals. Oscillations would then tend to inhibit the aggregation of the few hundred water molecules involved in the early crystal growth (see, for example, reference [48]).

Second, the low-frequency acoustic waves from the oscillating particles may radiate outwards from the magnetite-containing cells. Unlike acoustic waves from outside the object (which can trigger ice crystal nucleation), acoustic waves close to the oscillating ferromagnetic particles can dissipate rapidly into the surrounding tissue with spatially large gradients. These gradients may act to disrupt the aggregates of water molecules that organize into ice crystal nucleation structures [(see, for example, reference 48]) by differentially shearing them apart.

In either of these situations, the mechanical coupling of the ferromagnetic clusters to the surrounding cytoplasm would be an important feature for transducing the magnetic energy to the adjacent tissue. According to the present disclosure, the magnetic exposure conditions of these freezers could be tailored to maximize the coupling of biological magnetite for this transduction; the existing literature is not hypothesis-driven to the point where this has been attempted.

Moreover, in past studies of the magnetostatic bacteria, it has been noticed that linear strings of magnetosome chains collapse rapidly into clumps after cell death (see, for example, reference [49]). Elongated distributions of ferromagnetic particles, with their higher effective surface area and larger magnetic moments, can be more effective, relative to spherical clumps of particles, for transducing magnetostatic energy to acoustic waves. Detailed analysis of rock-magnetic properties of animal tissues imply that very similar post-mortem effects operate in those cellular environments as well, as measured by increasing interparticle magnetic interaction effects (see, for example, references [26,29]).

According to the present disclosure, the application of a moderately strong static magnetic field can act to inhibit the collapse of magnetosome chains during the freezing process, and thereby enhance the efficiency of energy transduction from the magnetic field to acoustic waves. It might even be possible to force particle assemblages that have already clumped to re-assemble into linear chains by exposing them to a strong external DC field, and gently tickling the crystals so that they move relative to each other. This would remove them from the pool of nucleation sites, and enhance their magnetic interaction with the external fields. Such 'tickling' could be done either ultrasonically, or by the application of an AC (oscillating) magnetic field aligned perpendicular to the DC (static) field. In some embodiments, having an AC field perpendicular to the DC field can be advantageous as the DC field aligns the magnetosome chains in one direction, and the AC field can vibrate the particles constituting the chain in a direction perpendicular to the alignment direction. For example, the particles may be in close contact and therefore vibrating in the direction of alignment might be impeded.

In an earlier study (see, for example, reference [49]), it was calculated that static magnetic fields of at least 15 mT would be needed to inhibit magnetosome chain collapse from the bacterium, *M. magnetotacticum*. Such a result was verified experimentally with transmission electron microscopy (TEM) that applied fields stronger than this and were indeed effective.

Magnetic oscillations during cooling could be achieved by applying the low-frequency AC magnetic fields perpendicular to the static magnetic field, with suitable amplitude (for example, 10% of the static field) to ensure substantial physical motion. In principle, detailed studies of the crystal size and shapes of biological magnetite produced in target tissues can help determine the best magnetic conditions for inhibiting magnetosome chain collapse and oscillation for each tissue.

If the oscillating magnetic component and the background magnetic field are in the same plane, the magnetic particles will briefly be at rest with regard to the background liquid twice during each oscillation cycle. When at rest, ice crystals are more likely to nucleate. Making the oscillating magnetic component wobble in the $3^{rd}$ dimension (elliptically or circularly in a plane perpendicular to the static field) will eliminate these transient pauses, and hence further inhibit the chance of nucleation. Such specific use of circularly polarized oscillating magnetic fields is not present in the previous literature.

According to the present disclosure, cryopreservation of important animal tissue cells like blood, sperm, or even small embryos could be enhanced by the addition of stabilized ferromagnetic particles like bacterial magnetosomes to the liquid media, providing more distributed sites for this magnetoacoustic transduction to occur.

As noted above, ferromagnetic particles tend to clump together into large aggregates that may not be a very effective transducer of magnetic oscillations. As known to the person skilled in the art that, in some embodiments, it may be necessary to coat synthetic particles with something to prevent clumping, as is done routinely in the preparation of ferrofluids. Understanding the underlying physical principles of how (and if) CAS technology works is an important step for improving the process of cryopreservation.

Figure 1:
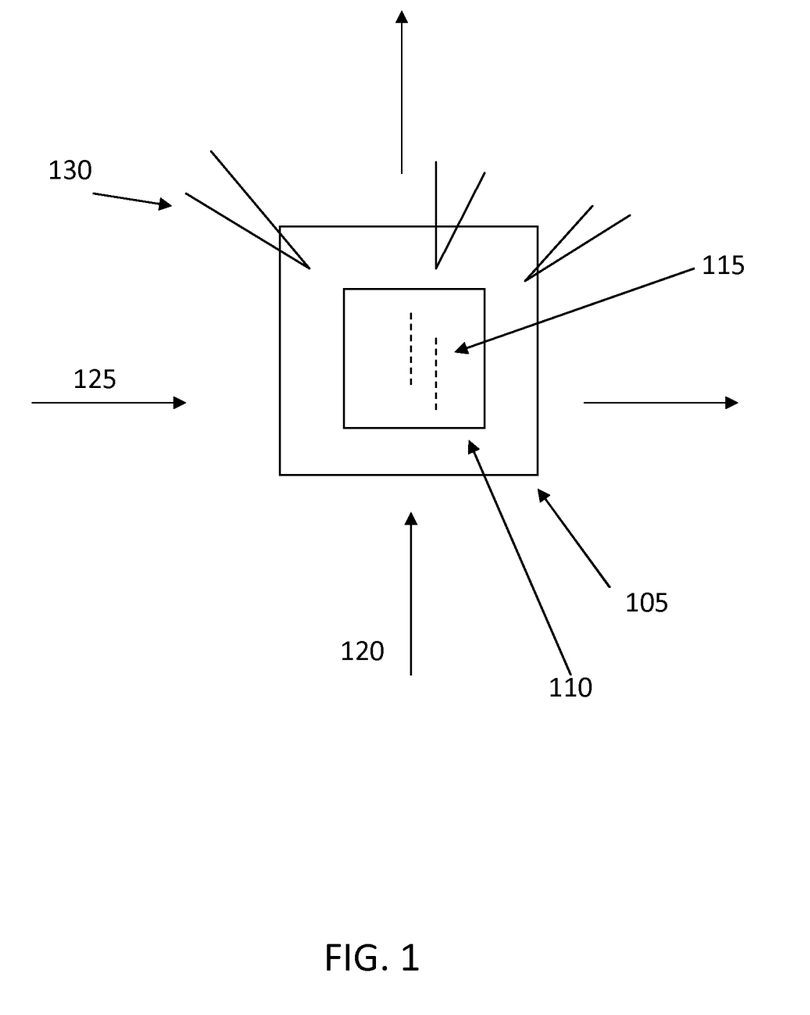
FIG. 1 illustrates an exemplary freezing container with magnetic fields.

According to an exemplary embodiment of the present disclosure, FIG. 1 illustrates an exemplary container (105) wherein a biological tissue (110) is placed. The biological tissue contains magnetic particles (115), either naturally or artificially introduced. A DC magnetic field is applied (120) aligning the magnetic particles (115). An AC magnetic field is applied (125) perpendicular to the DC field (120). In some embodiments, needle-shaped electrodes (130) may be present to apply a voltage between the biological tissue and the electrode in order to produce ions. For example, an electrode may be present in the container in contact with the biological tissues, in order to provide a way to apply a voltage difference between the needles and the tissues. Alternatively, the biological tissue may be simply left at the voltage level of the container (for example, the ground level), and a voltage may be applied to the needles.

Figure 2:
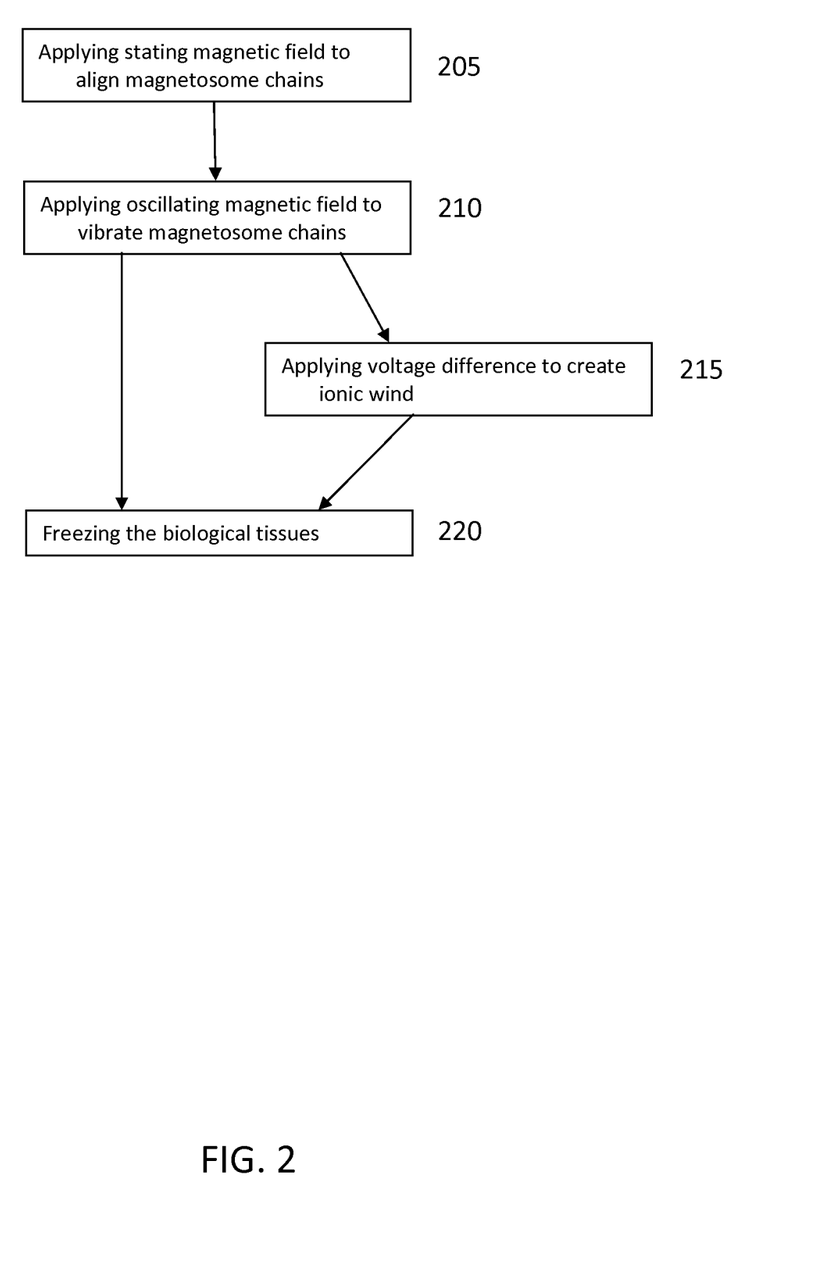
FIG. 2 illustrates an exemplary method for freezing tissues.

According to an exemplary embodiment of the present disclosure, FIG. 2 illustrates an exemplary method for freezing tissues: aligning magnetic particles in the biological tissues by applying a static magnetic field to the biological tissues in the container (205); vibrating the magnetic particles in the biological tissues by applying an oscillating magnetic field to the biological tissues in the container, wherein the oscillating magnetic field is perpendicular to the static magnetic field and oscillates around it in 2 or 3-dimensions (210); freezing the biological tissues while the static and oscillating magnetic fields are active (220). In some embodiments, a voltage may be applied with needle-shaped electrodes to create an ionic wind (215).

The exemplary method of FIG. 2 may also comprise additional steps. For example, magnetic particles may be introduced in the biological tissues prior to freezing, and orthogonal coils driven with sinusoidally-oscillating fields phased to produce a resultant field vector that oscillates in 3 dimensions.

In the present disclosure, a freezing element is any apparatus configured to freeze the biological tissues in the container, and can be referred to, for example, as a freezer.

In the present disclosure, air boundary layer refers to the layer of air that surrounds a sample to be frozen.

In the present disclosure, applying an electric field to the biological tissues in the container can refer to, for example, the method of surrounding the biological tissues with needle electrodes, to which a voltage is applied. As a result, when a voltage difference is created between the tissues and the electrode, an electric field is applied to the tissues.

Several references have been introduced in the present disclosure, referred to above, and listed below. The disclosure of all such references is incorporated herein by reference in its entirety.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

REFERENCES

[1] M. Kaku, T. Kawata, S. Abedini, H. Koseki, S. Kojima, H. Sumi, H. Shikata, M. Motokawa, T. Fujita, J. Ohtani, N. Ohwada, M. Kurita, and K. Tanne, Electric and magnetic fields in cryopreservation: A response. Cryobiology 64 (2012) 304-305.

[2] N. Owada, and S. Kurita, Super-quick freezing method and apparatus therefor. in: U.S.p. office, (Ed.), U.S. Pat. No. 6,250,087 B1, ABI Limited, Chiba, Japan, United States of America, 2001.

[3] N. Owada, and S. Saito, Quick freezing apparatus and quick freezing method. in: U.S.p. office, (Ed.), U.S. Pat. No. 7,810,340 B2, Owada, N., United States of America, 2010, pp. 15.

[4] S. Y. Lee, G. W. Huang, J. N. Shiung, Y. H. Huang, J. H. Jeng, T. F. Kuo, J. C. Yang, and W. C. V. Yang, Magnetic Cryopreservation for Dental Pulp Stem Cells. Cells Tissues Organs 196 (2012) 23-33.

[5] S. Abedini, M. Kaku, T. Kawata, H. Koseki, S. Kojima, H. Sumi, M. Motokawa, T. Fujita, J. Ohtani, N. Ohwada, and K. Tanne, Effects of cryopreservation with a newly-developed magnetic field programmed freezer on periodontal ligament cells and pulp tissues. Cryobiology 62 (2011) 181-187.

[6] P. Y. Lin, Y. C. Yang, S. H. Hung, S. Y. Lee, M. S. Lee, M. Chu, and S. M. Hwang, Cryopreservation of human embryonic stem cells by a programmed freezer with an oscillating magnetic field. Cryobiology 66 (2013) 256-260.

[7] M. Naito, S. Hirai, M. Mihara, H. Terayama, N. Hatayama, S. Hayashi, M. Matsushita, and M. Itoh, Effect of a Magnetic Field on Drosophila under Supercooled Conditions. Plos One 7 (2012).

[8] M. Kaku, H. Kamada, T. Kawata, H. Koseki, S. Abedini, S. Kojima, M. Motokawa, T. Fujita, J. Ohtani, N. Tsuka, Y. Matsuda, H. Sunagawa, R. A. M. Hernandes, N. Ohwada, and K. Tanne, Cryopreservation of periodontal ligament cells with magnetic field for tooth banking. Cryobiology 61 (2010) 73-78.

[9] B. Wowk, Electric and magnetic fields in cryopreservation. Cryobiology 64 (2012) 301-303.

[10] T. Suzuki, Y. Takeuchi, K. Masuda, M. Watanabe, R. Shirakashi, Y. Fukuda, T. Tsuruta, K. Yamamoto, N. Koga, N. Hiruma, J. Ichioka, and K. Takail, Experimental Investigation of Effectiveness of Magnetic Field on Food Freezing Process. Transactions of the Japan Society of Refrigerating and Air Conditioning Engineers 26 (2009) 371-386.

[11] A. K. Kobayashi-Kirschvink, and J. L. Kirschvink, Electrostatic enhancement of industrial drying processes. Ind. Engin. Chem. Proc. Design & Develop. 25 (1986) 1027-1030.

[12] S. P. Burke, Heat Transfer. in: U.P. Office, (Ed.), Combustion Utilities Corporation, New Yori, N.Y., United States of America, 1931, pp. 6.

[13] R. B. Bird, W. E. Stewart, and E. N. Lightfoot, Transport Phenomena, John Wiley & Sons, New York, 1960.

[14] H. Y. Choi, Electrohydrodamic condensation heat transfer. Journal of Heat Transfer 90 (1968) 98-102.

[15] P. H. G. Allen, Electric stress and heat transfer. British Journal of Applied Physics 10 (1959) 347-351.

[16] P. S. Lykoudis, and C. P. Yu, The influence of electrostrictive forces in natural thermal convection. International Journal of Heat and Mass Transfer 6 (1963) 853-862.

[17] R. Kronig, and N. Schwarz, On the theory of heat transfer from a wire in an electric field. Applied Scientific Research Section a-Mechanics Heat Chemical Engineering Mathematical Methods 1 (1947) 35-46.

[18] J. D. Cobine, Other Electrostatic Effects and Applications. in: A. D. Moore, (Ed.), Electrostatics and Its Applications, Wiley, New York, 1973, pp. 441-455.

[19] M. Robinson, Convective heat transfer at the surface of a corona electrode. International Journal of Heat and Mass Transfer 13 (1970) 263-274.

[20] E. Bonjour, J. Verdier, and L. Weil, Electroconvection effects on heat transfer. Chem. Eng. Prog. 58 (1962) 63-66.

[21] R. K. Adair, Constraints on biological effects of weak extremely-low frequency electromagnetic fields. Phys. Rev. A. 43 (1991) 1039-1048.

[22] J. L. Kirschvink, Constraints on biological effects of weak extremely low-frequency electromagnetic fields comment. Phys. Rev. A. 46 (1992) 2178-2184.

[23] J. L. Gould, J. L. Kirschvink, and K. S. Deffeyes, Bees have magnetic remanence. Science 201 (1978) 1026-1028.

[24] H. A. Lowenstam, Magnetite in denticle capping in recent chitons (polyplacophora). Geol. Soc. Am. Bull. 73 (1962) 435-438.

[25] C. Walcott, J. L. Gould, and J. L. Kirschvink, Pigeons have magnets. Science 205 (1979) 1027-1029.

[26] M. M. Walker, T. P. Quinn, J. L. Kirschvink, and T. Groot, Production of single-domain magnetite throughout life by sockeye salmon, *Oncorhynchus nerka*. J. Exptl. Biol. 140 (1988) 51-63.

[27] J. L. Kirschvink, D. S. Jones, and B. J. McFadden, Magnetite Biomineralization and Magnetoreception in Organisms: A New Biomagnetism, Plenum Press, New York, N.Y., 1985.

[28] M. M. Walker, J. L. Kirschvink, S.-B. R. Chang, and A. E. Dizon, A candidate magnetic sense organ in the Yellowfin Tuna *Thunnus albacares*. Science 224 (1984) 751-753.

[29] M. M. Walker, J. L. Kirschvink, and A. E. Dizon, Magnetoreception and Magnetite Biomineralization in Fish. in: J. L. Kirschvink, D. S. Jones, and B. McFadden, (Eds.), Magnetite Biomineralization and Magnetoreception in Organisms: A New Biomagnetism, Plenum Press, New York, N.Y., 1985, pp. 417-437.

[30] F. Brem, A. M. Hirt, M. Winklhofer, K. Frei, Y. Yonekawa, H. G. Wieser, and J. Dobson, Magnetic iron compounds in the human brain: a comparison of tumour and hippocampal tissue. Journal of the Royal Society Interface 3 (2006) 833-841.

[31] J. F. Collingwood, R. K. K. Chong, T. Kasama, L. Cervera-Gontard, R. E. Dunin-Borkowski, G. Perry, M. Posfai, S. L. Siedlak, E. T. Simpson, M. A. Smith, and J. Dobson, Three-dimensional tomographic Imaging and characterization of iron compounds within Alzheimer's plaque core material. Journal of Alzheimers Disease 14 (2008) 235-245.

[32] J. R. Dunn, M. Fuller, J. Zoeger, J. Dobson, F. Heller, J. Hammann, E. Caine, and B. M. Moskowitz, Magnetic material in the Human hippocampus. Brain Research Bulletin 36 (1995) 149-153.

[33] P. P. GrassiSchultheiss, F. Heller, and J. Dobson, Analysis of magnetic material in the human heart, spleen and liver. Biometals 10 (1997) 351-355.

[34] D. Hautot, Q. A. Pankhurst, and J. Dobson, Superconducting quantum interference device measurements of dilute magnetic materials in biological samples. Review of Scientific Instruments 76 (2005).

[35] D. Hautot, Q. A. Pankhurst, C. M. Morris, A. Curtis, J. Burn, and J. Dobson, Preliminary observation of elevated levels of nanocrystalline iron oxide in the basal ganglia of neuroferritinopathy patients. Biochimica Et Biophysica Acta-Molecular Basis of Disease 1772 (2007) 21-25.

[36] Q. Pankhurst, D. Hautot, N. Khan, and J. Dobson, Increased levels of magnetic iron compounds in Alzheimer's Disease. Journal of Alzheimers Disease 13 (2008) 49-52.

[37] J. L. Kirschvink, and J. L. Gould, Biogenic magnetite as a basis for magnetic field sensitivity in animals. Bio Systems 13 (1981) 181-201.

[38] J. L. Kirschvink, M. M. Walker, and C. Deibel, Magnetite-based Magnetoreception. Current Opinion in Neurobiology 11 (2001) 462-467.

[39] J. L. Kirschvink, A. Kobayashi, and B. J. Woodford, Magnetite biomineralization in the human brain. Proceedings of the National Academy of Sciences 89 (1992) 7683-7687.

[40] J. Dobson, and P. Grass, Magnetic properties of human hippocampal tissue—evaluation of artefact and contamination sources. Brain Research Bulletin 39 (1996) 255-259.

[41] A. Kobayashi, and J. L. Kirschvink, Magnetoreception and EMF Effects: Sensory Perception of the geomagnetic field in Animals & Humans. in: M. Blank, (Ed.), Electromagnetic Fields: Biological Interactions and Mechanisms, American Chemical Society Books, Washington, D.C., 1995, pp. 367-394.

[42] A. K. Kobayashi, N. Yamamoto, and J. L. Kirschvink, Studies of inorganic crystals in biological tissue—magnetite in the Human Body. J. Japanese Society of Powder and Powder metallurgy 43 (1996) 1354-1360.

[43] A. K. Kobayashi, N. Yamamoto, and J. L. Kirschvink, Studies of inorganic crystals in biological tissue—magnetite in human tumor. J. Japanese Society of Powder and Powder metallurgy 44 (1997) 294-300.

[44] A. K. Kobayashi, J. L. Kirschvink, and M. H. Nesson, Ferromagnets and EMFs. Nature 374 (1995) 123-123.

[45] M. M. Walker, J. L. Kirschvink, A. S. Perry, and A. E. Dizon, Methods and Techniques for the Detection, Extraction, and Characterization of Biogenic Magnetite. in: J. L. Kirschvink, D. S. Jones, and B. J. McFadden, (Eds.), Magnetite Biomineralization and Magnetoreception in Organisms: A New Biomagnetism, Plenum Press, New York, 1985, pp. 154-166.

[46] J. L. Kirschvink, Rock Magnetism linked to Human Brain Magnetite. EOS, Trans. Am. Geophysical Union 75 (1994) 178-179.

[47] S. H. K. Eder, H. Cadiou, A. Muhamad, P. A. McNaughton, J. L. Kirschvink, and M. Winklhofer, Magnetic characterization of isolated candidate vertebrate magnetoreceptor cells. Proceedings of the National Academy of Sciences of the United States of America 109 (2012) 12022-12027.

[48] E. B. Moore, and V. Molinero, Structural transformation in supercooled water controls the crystallization rate of ice. Nature 479 (2011) 506-U226.

[49] A. Kobayashi, J. L. Kirschvink, C. Z. Nash, R. E. Kopp, D. A. Sauer, L. E. Bertani, W. F. Voorhout, and T. Taguchi, Experimental observation of magnetosome chain collapse in magnetotactic bacteria: Sedimentological, paleomagnetic, and evolutionary implications. Earth and Planetary Science Letters 245 (2006) 538-550.

[50] D. Gunders, Wasted: How America is Losing Up to 40 Percent of Its Food from Farm to Fork to Landfill, NRDC Issue Paper Natural Resources Defense Council, 2012.

What is claimed is:

1. A system to freeze biological tissues, the system comprising:
   a) a container, configured to contain biological tissues;
   b) a static magnetic field generator, configured to apply a static magnetic field to the biological tissues in the container;
   c) an oscillating magnetic field generator, configured to apply an oscillating magnetic field to the biological tissues in the container;
   d) a freezing element, configured to freeze the biological tissues in the container; and
   e) at least one electrode configured to apply a voltage to the biological tissues inside the container, the at least one electrode having a shape of a needle and being configured to produce ions at an air boundary layer adjacent to a surface of the biological tissues in the container.

2. The system of claim 1, wherein the oscillating magnetic field is applied perpendicularly to the static magnetic field in one or two dimensions.

3. A system to freeze biological tissues, the system comprising:
   a) a container, configured to contain biological tissues:
   b) a static magnetic field generator, configured to apply a static magnetic field to the biological tissues in the container;
   c) an oscillating magnetic field generator, configured to apply an oscillating magnetic field to the biological tissues in the container, the magnetic field applied perpendicularly to the static magnetic field in one or two dimensions; and
   d) a freezing element, configured to freeze the biological tissues in the container, wherein the intensity of the oscillating magnetic field is 10% of the intensity of the static magnetic field.

4. The system of claim 1, wherein the intensity of the static magnetic field is greater than 15 mT.

5. A method to freeze biological tissues, the method comprising:
   i) providing a system comprising:
   a) a container, configured to contain biological tissues;
   b) a static magnetic field generator, configured to apply a static magnetic field to the biological tissues in the container;
   c) an oscillating magnetic field generator, configured to apply an oscillating magnetic field to the biological tissues in the container;
   d) a freezing element, configured to freeze the biological tissues in the container; and
   e) at least one electrode configured to apply a voltage to the biological tissues inside the container, the at least one electrode having a shape of a needle and being configured to produce ions at an air boundary layer adjacent to a surface of the biological tissues in the container;
   ii) applying a static magnetic field to the biological tissues in the container;
   iii) applying an oscillating magnetic field to the biological tissues in the container; and
   iv) freezing the biological tissues in the container.

6. The method of claim 5, wherein the oscillating magnetic field is applied perpendicularly to the static magnetic field.

7. The method of claim 5, wherein an intensity of the static magnetic field is greater than 15 mT.

8. The method of claim 5, wherein the intensity of the oscillating magnetic field is 10% of the intensity of the static magnetic field.

9. The method of claim 5, further comprising introducing magnetic particles into the biological tissues prior to freezing.

10. A method to freeze biological tissues, the method comprising:
- i) providing a system comprising:
  - a) a container, configured to contain biological tissues;
  - b) a static magnetic field generator, configured to apply a static magnetic field to the biological tissues in the container;
  - c) an oscillating magnetic field generator, configured to apply an oscillating magnetic field to the biological tissues in the container, the magnetic field applied perpendicularly to the static magnetic field in one or two dimensions: and
  - d) a freezing element configured to freeze the biological tissues in the container, wherein the intensity of the oscillating magnetic field is 10% of the intensity of the static magnetic field;
- ii) applying a static magnetic field to the biological tissues in the container;
- iii) applying an oscillating magnetic field to the biological tissues in the container;
- iv) applying an electric field to the biological tissues in the container; and
- v) freezing the biological tissues in the container.

11. The method of claim 10, wherein the oscillating magnetic field is applied perpendicularly to the static magnetic field.

12. The method of claim 10, wherein an intensity of the static magnetic field is greater than 15 mT.

\* \* \* \* \*